United States Patent [19]

Shimomura et al.

[11] 4,210,669
[45] Jul. 1, 1980

[54] PROSTANOIC ACID DERIVATIVES

[75] Inventors: Hiromi Shimomura, Nishinomiya; Akihiko Sugie, Takarazuka; Junki Katsube, Toyonaka, all of Japan

[73] Assignee: Sumitomo Chemical Company, Limited, Osaka, Japan

[21] Appl. No.: 911,039

[22] Filed: May 30, 1978

[30] Foreign Application Priority Data

May 31, 1977 [JP] Japan .................................. 52-64217
Sep. 6, 1977 [JP] Japan ................................. 52-107642

[51] Int. Cl.² .................. C07C 177/00; A61K 31/19; A61K 31/215
[52] U.S. Cl. .......................... 424/305; 260/343.3 P; 260/346.22; 260/464; 560/121; 562/503; 424/317
[58] Field of Search ................. 424/305, 317; 560/121; 562/503

[56] References Cited

PUBLICATIONS

Corey et al, J. Am. Chem. Soc. 92,397 (1970).

Primary Examiner—Robert Gerstl
Attorney, Agent, or Firm—Stevens, Davis, Miller & Mosher

[57] ABSTRACT

Prostanoic acid derivatives of the formula,

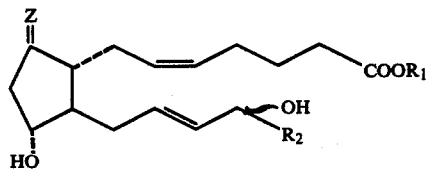

[I]

wherein $R_1$ is hydrogen or $C_{1-4}$ alkyl, $R_2$ is $C_{4-8}$ alkyl and $>C=Z$ is $>C=O$ or

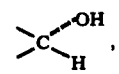

are prepared by reacting a cyclopentane of the formula,

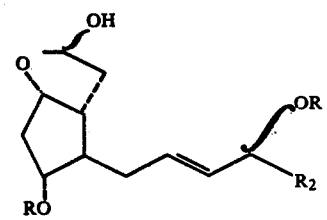

wherein $R_2$ is defined above and R is hydrogen or tetrahydropyranyl, with Wittig reagent of the formula,

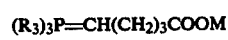

$(R_3)_3P=CH(CH_2)_3COOM$ wherein $R_3$ is aryl and M is alkali metal and, if necessary, hydrolyzing, or by oxidizing a compound of the formula,

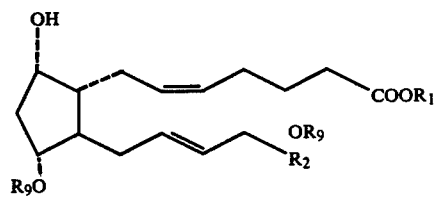

wherein $R_1$ and $R_2$ are as defined above and $R_9$ is tetrahydropyranyl group, with an oxidizing agent. The compounds (I) are useful as anti-ulcer agent.

3 Claims, No Drawings

PROSTANOIC ACID DERIVATIVES

The present invention relates to prostanoic acid derivatives, to intermediates for their preparation and their production and use.

More particularly, this invention relates to prostanoic acids, to cyclopentylacetic acids and to a process for preparation thereof.

One of the purpose of this invention is to provide prostanoic acids of the formula (I):

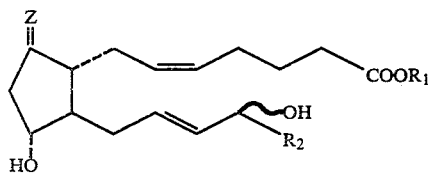

[I]

wherein $R_1$ is hydrogen atom or $C_{1-4}$ alkyl group, $R_2$ is $C_{4-8}$ alkyl and $>C=Z$ is $>C=O$ or

.

Another purpose of this invention is to provide cyclopentylacetic acids of the formula (II);

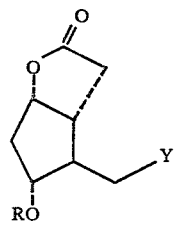

[II]

wherein R is hydrogen atom or a hydroxy-protecting group and Y is CHO, CH=CHCOR_2 or

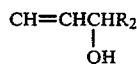

(wherein $R_2$ is defined above).

In the significances as used above, "$C_{1-4}$ alkyl" means an alkyl group having from one to four carbon atoms (e.g., methyl, ethyl, isopropyl, t-butyl). "$C_{4-8}$ alkyl" means a straight or branched alkyl group having from four to eight carbon atoms (e.g., pentyl, butyl, α-methyl-n-pentyl).

Preferred examples of an hydroxy-protecting group are an acyl group such as acetyl, propionyl, benzoyl, and p-phenylbenzoyl.

The prostanoic acids (I) of this invention have various useful pharmacological activities and are useful as antiulcer agents and gastric secretion inhibitors.

It has now been found that the prostanoic acids of the formula (I) possess anti-gastrointestinal ulcer activity. That is, they inhibit an excessive secretion of gastric acid, and thereby inhibit formation of a gastro-intestinal ulcer or heal the ulcer in mammals.

The cyclopentylacetic acids of the formula (II) are valuable intermediates for producing the prostanoic acids (I) as above.

The novel prostanoic acids (I) of the present invention can be prepared by the following methods: The prostanoic acids of the formula [Ia]

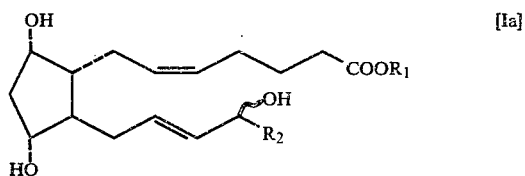

[Ia]

wherein $R_1$ and $R_2$ are defined above, can be prepared by reacting the compound of the formula (III);

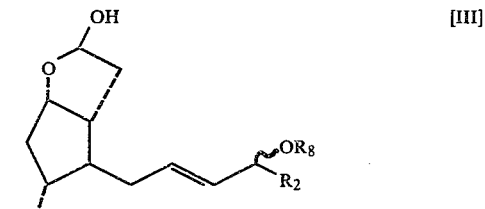

[III]

wherein $R_2$ is as defined above and $R_8$ is hydrogen or tetrahydropyranyl, with a compound of the formula (IV);

$(R_3)_3P=CH(CH_2)_3COOM$  [IV]

wherein $R_3$ is an aryl and M is an alkali metal and, if necessary, subsequently esterifying and depyranylating the resulting products. The Wittig reaction can be carried out in the presence of solvent using 1–10 equivalent (preferably 2–4 equivalent) of the Wittig reagent (IV). Examples of the solvent are ethers (e.g., diethylether, tetrahydrofuran, dioxane), hydrocarbons (e.g., benzene, toluene, hexane) and dimethyl sulfoxide.

The reaction can be effected ordinarily at room temperature, but it can be controlled with warming or cooling depending upon the extent of the progress. The reaction time may vary depending upon the reaction temperature and the reagent to be used therein but is generally 2-30 hrs.

The prostanoic acid thus obtained can be separated from the reaction mixture and the prostanoic acid thus obtained, if $R_1$ is $C_{1-4}$ alkyl, can be esterified and, if $R_8$ is tetrahydropyranyl, can be hydrolyzed and purified by conventional procedures. The prostanoic acid of the formula [Ib];

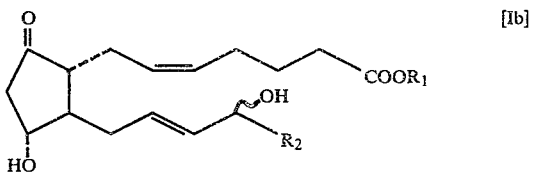

[Ib]

wherein $R_1$ and $R_2$ are as defined above, can be prepared by oxidizing a prostanoic acid of the formula [Ic];

[Ic]

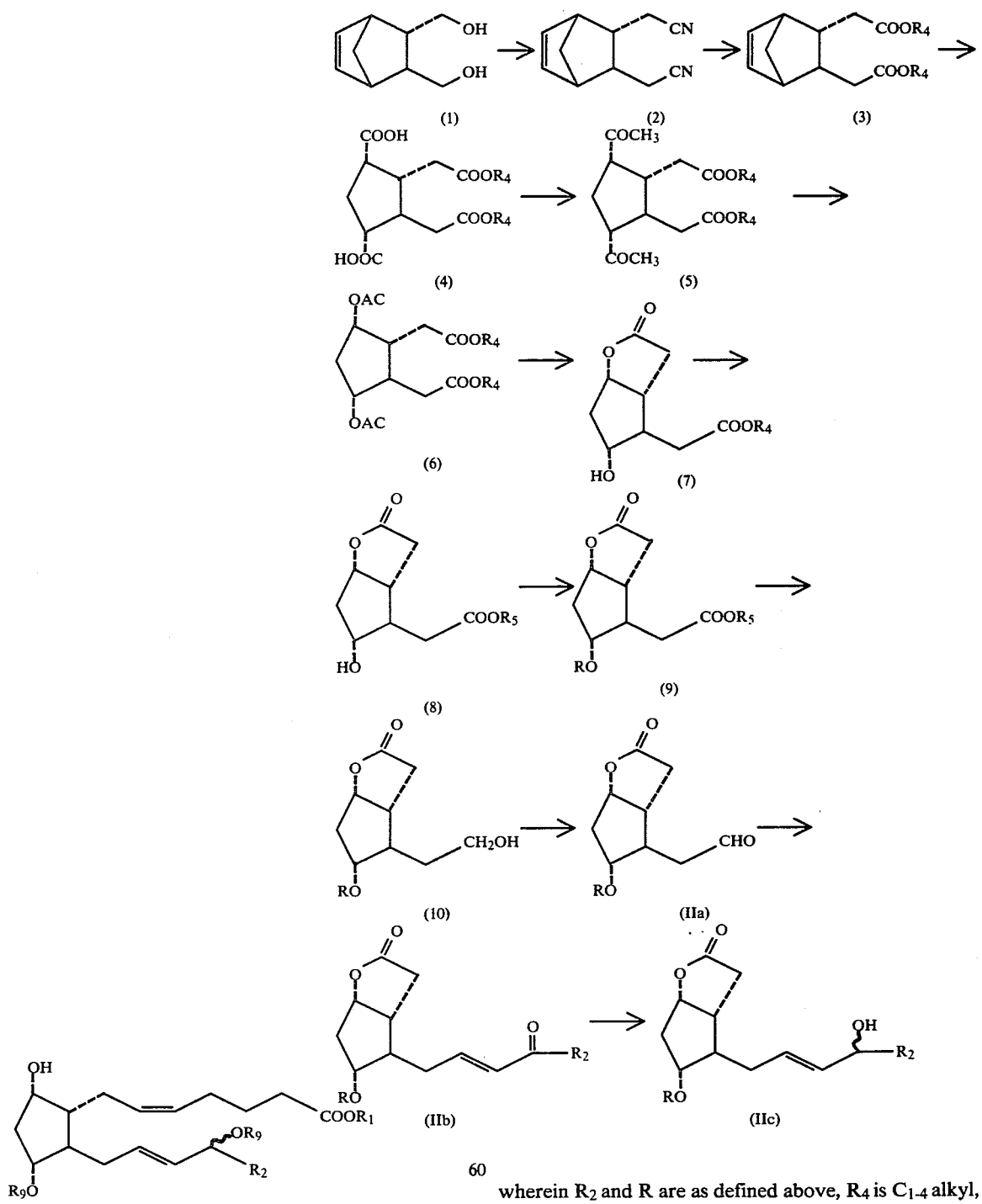

wherein $R_1$ and $R_2$ are as defined above and $R_9$ is tetrahydropyranyl group, with an oxidizing agent.

As to the oxidizing agent to be used in this reaction, Collins reagent ($CrO_3$-dipyridine) and Moffatt reagent (e.g., dimethyl sulfoxide-dicyclohexylcarbodiimide-pyridine-trifluoroacetic acid) are preferable. The reaction can be carried out by the same procedures as described in J. Am. Chem. Soc., 96 5876–5893 (1974). The novel cyclopentylacetic acids (II) of the invention can be prepared by the following methods;

Method A:

wherein $R_2$ and $R$ are as defined above, $R_4$ is $C_{1-4}$ alkyl, Ac is acetyl and $R_5$ is phenacyl group.

The compound (3) is obtained from the compound (1) by a sequence of tosylation, cyanation, hydrolysis and esterification. The transformation of the compound (3) to the compound (5) is conducted by oxidation, chlorination, diazotization and reduction. The Baeyer-Villiger oxidation of the compound (5) gives the diacetoxy compound (6). Acid hydrolysis of the compound (6) gives the lactone-carboxylic acid (7). The compound (7) is treated with phenacyl halide derivative to give the compound (8).

Acylation of the compound (8) gives the compound (9). The transformation of the compound (9) to the compound (10) can be conducted by dephenacylation and reduction substantially, by the same procedures as disclosed in Tetrahedron Letters No. 19, 1629–1632 (1977).

This reaction can be carried out by conventional procedures as disclosed, for example, in J. Am. Chem. Soc., 96, 5876–5893 (1974).

The compound (IIc) can be obtained by the reduction of the compound (IIb) with reducing agents such as alkali borohydride (e.g., sodium borohydride) aluminium alkoxide (e.g., aluminium triisopropoxide), in a conventional manner.

Method B:

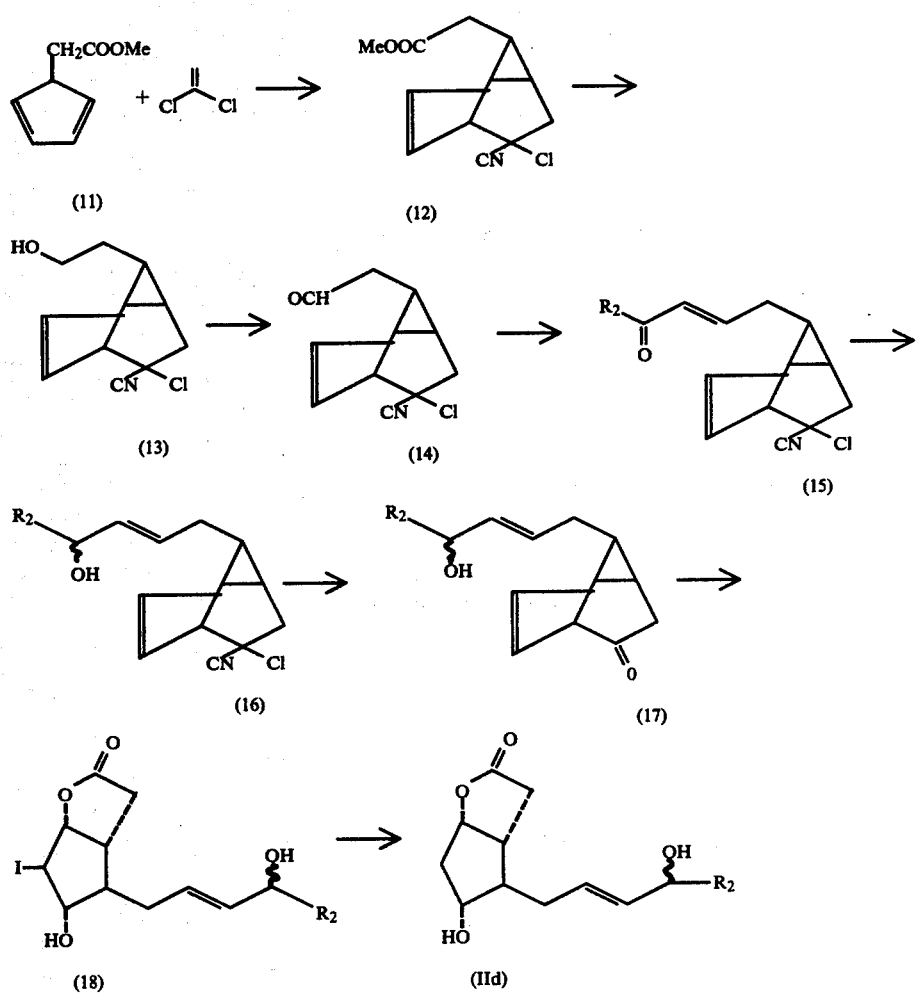

The compound (IIa) can be obtained by oxidizing the compound (10). The oxidation of the compound (10) to the compound (IIa) can be carried out in the same manner as the oxidation of the compound (Ie) into the compound (Ib).

The compound (IIb) is obtained from the compound (IIa) by reacting the compound (IIa) with the ylid of the following formula (V).

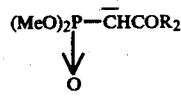 (V)

wherein $R_2$ is as defined above.

wherein $R_2$ is as defined above.

The Diels-Alder reaction of cyclopentadiene derivative (11) with α-chloroacrylonitrile at 0° C. gives the norbornene derivative (12), which is reduced with calcium borohydride to give alcohol derivative (13).

The compound (13) is oxidized with Collins-reagent ($CrO_3$-2pyridine) to give the aldehyde (14) followed by reacting with the ylid of the compound (V),

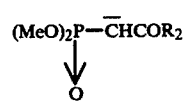 (V)

wherein $R_2$ is as defined above, to give the enone (15).

The transformation from the compound (15) to the compound (17) is conducted by reduction and alkaline hydrolysis. The compound (17) is treated with alkaline hydrogen peroxide solution to give the iodo-lactone derivative (18).

The compound (18) is treated with tributyltin hydride to give the compound (IId).

The cyclopentylacetic acid of the following formula (III);

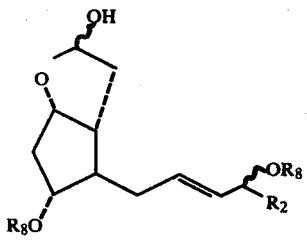

wherein $R_8$ and $R_2$ are as defined above, may be prepared by the following method: The cyclopentylacetic acid of the formula (IId)

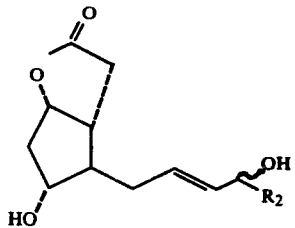

wherein $R_2$ is as defined above, which is obtained by the method B or hydrolysis of the compound of the formula (IIc) in the method A,

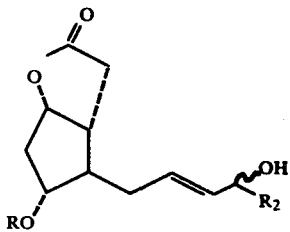

is treated with diisobutylaluminium hydride to give the compound (III). ($R_8$ is hydrogen).

Furthermore the compound (IId) is treated with dihydropyrane followed by reduction with diisobutyl aluminium hydride to give the compound (III). ($R_8$ is tetrahydropyranyl).

The novel prostanoic acid of this invention may be administered effectively orally, sublingnally, or intravenously at a daily dosage of about 1 to 100 mg/kg as gastric secretion inhibitors and antiulcers.

The following examples are given for the purpose of illustration and it is not intended to limit the invention.

Experiment

EXAMPLE 1 exo-2-Cyanomethyl-endo-3-cyanomethylbicyclo[2,2,1]hept-5-ene.

To a solution of exo-2-hydroxymethyl-endo-3-hydroxymethylbicyclo[2,2,1]hept-5-ene (3.08 g) in pyridine (10 ml), was added a solution of p-toluenesulfonyl chloride (7.7 g) in dry benzene (10 ml) at 0° C. After stirring overnight at room temperature, benzene (100 ml) was added to this solution. The organic layer was separated and washed with water, 10% hydrochloric acid, aqueous sodium bicarbonate and water and then dried over magnesium sulfate. Evaporation of the solvent gave the crystalline ditosylate compound (9.0 g).

To a solution of this tosylate (9.0 g) in anhydrous dimethyl sulfoxide, was added sodium cyanide (4 g) and heated at 100° C. for 1.5 hr.

Benzene and water was added to the reaction mixture and, after equilibration, the organic layer was washed with water, dried, and evaporated to give an objective dicyano compound (3.1 g) as an oil.

$IR\nu_{max}^{film}$ cm$^{-1}$: 2950, 2250, 1420, 1340.

NMR (CCl$_4$)δ:6.0–6.5 (2H, m, olefinic protons).

EXAMPLE 2 exo-2-endo-3-Biscarbomethoxymethylbicyclo[2,2,1]hept-5-ene.

The cyano compound (10 g) obtained by the procedure of Example 1, was refluxed for 5 hr in 20% aqueous potassium hydroxide. The reaction mixture was acidified with 10% hydrochloric acid and extracted with ethyl acetate. The organic extract was washed with water, dried, and evaporated to give a crystalline dicarboxylic acid compound (m.p. 162° C.). This acid was dissolved in dry methanol and a few drops of concentrated sulfuric acid was added. After stirring overnight, the solution was neutralized with sodium bicarbonate and methanol was evaporated. The residue was extracted with benzene and the extract was distilled to give 9.5 g of the objective product (b.p., 106°–110° C./0.2 mmHg).

$IR\nu_{max}^{film}$ cm$^{-1}$: 1740, 1440, 1150.

NMR (CCl$_4$)Γ: 5.8–6.4 (2H, m), 3.65 (6H, S).

EXAMPLE 3

1-α-Acetyl-4-α-acetyl-2-α-carbomethoxymethyl-3-β-carbomethoxymethylcyclopentane.

The diester (10 g), prepared by the procedure of Example 2, was dissolved in dry benzene (200 ml) and then crown ether (dibenzo-18-crown-6) (500 mg) and potassium permanganate (22 g) was added. After stirring overnight at room temperature, water (50 ml) was added and stirred for another 30 minutes. The mixture was filtered and the benzene layer of the filtrate was separated. The aqueous phase was acidified with concentrated hydrochloric acid to pH 1, and was extracted with ethyl acetate. Evaporation of ethyl acetate gave 9.6 g of an objective dicarboxylic acid.

This acid (9.6 g) was suspended in dry benzene (150 ml) and dry dimethylformamide (1 ml), and then 20% phosgene in toluene solution (30 ml) was added with cooling.

The reaction mixture was stirred at room temperature and was concentrated under reduced pressure to give an acid chloride.

To an etheral solution of diazomethane, was added a solution to the acid chloride prepared above in ether and was stirred for 3 hr at room temperature.

Evaporation of ether gave a bis-diazoketone compound.

This diazoketone was dissolved in chloroform (70 ml) and treated with 50% hydroiodic acid (10 ml).

After equilibration, the chloroform layer was washed with water, dried and concentrated to give a crude oil, which was chromatographed on silica gel to afford an objective diacetyl compound (3.2 g).

IR$\nu_{max}^{film}$ cm$^{-1}$: 1740, 1710, 1440, 1360, 1260.

NMR (CCl$_4$)δ: 3.6 (6H, S), 2.13 (6H, S).

EXAMPLE 4

1-α-Acetoxy-4-α-acetoxy-2-α-carbomethoxymethyl-3-β-carbomethoxymethyl-cyclopentane.

To a mixture of the diacetyl compound (1.5 g), prepared by the procedure of Example 3, in dichloromethane (60 ml) and disodium hydrogen phosphate (6.7 g), was added a solution of 90% hydrogen peroxide (1.28 ml) and trifluoroacetic anhydride (9.8 g) at a rate under gently reflux.

After stirring for 2 hr at room temperature, the reaction mixture was filtrated and washed with chloroform.

The filtrate was washed with aqueous sodium bicarbonate and water, dried and evaporated to give an objective diacetoxy compound (1.48 g) as an oil.

IR$\nu_{max}^{film}$ cm$^{-1}$: 1740, 1440, 1370, 1240, 1160, 1070, 1020.

NMR (CCl$_4$)δ: 4.7–5.3 (2H, m), 3.6 (6H, S), 2.0 (6H, S).

EXAMPLE 5

2,4-α,α-Dihydroxy-5-β-carboxymethylcyclopentyl-α-acetic acid γ-lactone.

1,4-α,α-Diacetoxy-2-α-carbomethoxymethyl-3-β-carbomethoxymethylcyclopentane (300 mg) obtained by the procedure of Example 4 was heated in concentrated hydrochloric acid (2.0 ml) for 2 hr. and evaporated under reduced pressure.

The residue was extracted with ether and concentrated to give a crystalline lactone (160 mg).

IR$\nu_{max}^{nujol}$ cm$^{-1}$: 1780, 1710, 1420, 1200, 1080, 1040

EXAMPLE 6

2-α-Hydroxy-4-acetoxy-5-β-carboxymethylcyclopentyl-α-acetic acid γ-lactone.

2,4-α,α-Dihydroxy-5-β-carboxymethylcyclopentyl-α-acetic acid γ-lactone (100 mg) prepared by the procedure of Example 5 was dissolved in water (2 ml) and an equivalent of 5% aqueous sodium hydroxide solution was added thereto.

A solution of p-bromophenacyl bromide (160 mg) in methanol (5 ml) was added to this solution.

After refluxing for 1.5 hr, the solvent was distilled off.

The residue was extracted with ethyl acetate, dried and concentrated to give an oily phenacyl ester (160 mg).

IR$\nu_{max}^{film}$ cm$^{-1}$: 1760, 1740, 1700, 1590, 1420, 1400, 1370, 1170

The phenacyl ester, prepared above, was acetylated with acetic anhydride (100 mg) in pyridine (2 ml).

After being chromatographed on silica gel, the objective acetate was obtained as an oil (155 mg).

IR$\nu_{max}^{film}$; cm$^{-1}$: 1770, 1740, 1700, 1590, 1420, 1400

The acetate compound prepared above was dissolved in acetic acid (10 ml) and zinc powder (1 g) was added.

After stirring for 2 hr at room temperature, the reaction mixture was filtered.

The filtrate was concentrated in vacuo and to the residue was added ether and aqueous sodium bicarbonate.

After equilibration, the aqueous phase was acidified with diluted sulfuric acid to pH 1 and extracted several times with dichloromethane.

Evaporation of the solvent gave a crystalline carboxylic acid (60 mg, m.p. 108°–110° C.).

IR$\nu_{max}^{nujol}$ cm$^{-1}$: 1770, 1740, 1710, 1440, 1340, 1230, 1180, 1040

EXAMPLE 7

2-α-Hydroxy-4-α-acetoxy-5-β-(2'-hydroxyethyl)-cyclopentyl-α-acetic acid γ-lactone.

2-α-Hydroxy-4-α-acetoxy-5-β-carboxymethylcyclopentyl-α-acetic acid γ-lactone (50 mg) prepared by the procedure of Example 6 was treated with excess diborane in tetrahydrofuran at 0°–10° C.

After 1 hr, the reaction mixture was quenched with acetone and evaporated in vacuo.

Chloroform and saturated aqueous ammonium chloride were added to this residue.

The organic layer was separated and evaporated to give an objective alcohol (45 mg) as an oil.

IR$\nu_{max}^{film}$ cm$^{-1}$:3450, 1770, 1730, 1360, 1240, 1160, 1020.

NMR (CCl$_4$)δ:4.8–5.2 (2H, m), 3.7 (2H, t), 2.0 (3H, S).

EXAMPLE 8

2-α-Hydroxy-4-α-acetoxy-5-β-(4-oxo-trans-2-noneyl)-cyclopentyl-α-acetic acid γ-lactone.

The alcohol compound (50 mg) prepared by the procedure of Example 7, was oxidized with chromic anhydride dipyridine complex in dichloromethane (10 ml) and then ether was added.

The reaction mixture was filtered and the filtrate was concentrated to give an objective formyl derivative as an oil.

This formyl compound was added at ambient temperature to the reagent prepared from dimethyl 2-oxoheptylphosphonate and 50% sodium hydride in dimethoxyethane.

After stirring for 2 hr, the reaction mixture was neutralized with acetic acid and evaporated.

The residue was extracted with ether and evaporation of ether gave an oil, which was chromatographed on silica gel, to afford an objective enone (65 mg).

IR$\nu_{max}^{film}$ cm$^{-1}$:1770, 1730, 1700, 1660, 1620, 1460, 1360, 1220, 1040.

EXAMPLE 9

2-α-Hydroxy-4-α-acetoxy-5-β-(4-hydroxy-trans-2-noneyl)cyclopentyl-α-acetic acid γ-lactone.

The enone compound (50 mg) prepared by the procedure of Example 8, was treated with sodium borohydride in methanol at 0° C.

The reaction mixture was quenched with acetone and evaporated.

To the residue, were added ether and aqueous ammonium chloride.

The ether extract was washed with water, dried and concentrated to give an objective alcohol (45 mg) as an oil.

IR$\nu_{max}^{film}$ cm$^{-1}$:3500, 1770, 1190, 1130, 1080.

EXAMPLE 10

2-Chloro-2-cyano-7-carbomethoxymethylbicyclo-[2,2,1]hept-5-ene.

2,4-Cyclopentadienyl acetic acid methyl ester was prepared from the sodium salt of cyclopentadiene and methyl bromoacetate in tetrahydrofuran by the method of J. J. Partridge [J. Am. Chem. Soc., 95, 7171 (1973)].

A solution of the diene obtained above in α-chloroacrylnitrile (5 ml) was added to a mixture of α-chloroacrylnitrill (10 ml) and anhydrous cupric fluoroborate (1.5 g) at 0° C. The reaction mixture was stirred for 20 hr at 0°–5° C.

The mixture was concentrated in vacuo and the oily residue obtained was dissolved in ether. The ether solution was washed with aqueous sodium tartarate and brine and then dried.

Evaporation of solvent gave a crude oily product which was chromatographed on silica gel using benzene as eluent to afford an objective adduct (3.8 g).

IR$\nu_{max}^{film}$ cm$^{-1}$: 2950, 2240, 1740, 1440, 1330, 1165.

NMR (CCl$_4$)δ: 6.33 (1H, d, d), 6.01 (1H, d, d), 3.63 (3H, s).

EXAMPLE 11

2-Chloro-2-cyano-7-(2-hydroxyethyl)bicyclo[2,2,1-]hept-5-ene.

An ethanol solution of the adduct (500 mg) prepared by the procedure of Example 10 was added to a mixture of four equivalent of sodium borohydride, three equivalent of powdered calcium chloride and ethanol (20 ml) at room temperature under nitrogen.

After stirring for 3 hr, the reaction mixture was quenched by adding aqueous ammonium chloride and was extracted with chloroform.

The organic layer was washed with brine, dried and evaporated to give an oily residue, which was chromatographed on silica gel to afford an objective alcohol (300 mg).

IR$\nu_{max}^{film}$ cm$^{-1}$: 3600, 3200, 2950, 2250, 1450, 1345, 1060.

NMR (CCl$_4$)δ: 6.28 (1H, d,d), 5.97 (1H, d,d).

EXAMPLE 12

2-α-Hydroxy-4-α-hydroxy-5-β-(4-hydroxy-trans-2-noneyl)cyclopentyl-α-acetic acid γ-lactone.

The acetoxy compound (150 mg) obtained by the procedure of Example 9 was dissolved in methanol (3 ml) and potassium carbonate (50 mg) was added to this solution. After stirring for 1 hr at room temperature, the reaction mixture was neutralized with 1 N hydrochloric acid and then evaporated in vaccuo. The residue was extracted with ethyl acetate. The extract was washed with brine and dried and then evaporated to give an oil, which was chromatographed on silica gel with benzene ethyl acetate (1:3) as an eluent.

The objective diol-lactone derivative (112 mg) was obtained as an oil.

IR$\nu_{max}^{film}$ cm$^{-1}$: 3400, 3060, 2950, 2850, 1770, 1460, 1380, 1340, 1260, 1180.

EXAMPLE 13

2-α-Hydroxy-4-α-tetrahydropyranyloxy-5-β-(4-tetrahydropyranyloxy-trans-2-nonenyl)cyclopentyl-α-acetic acid γ-lactone.

To a solution of the diol compound (110 mg) prepared by the procedure of Example 12 in methylene chloride (2 ml), were added 2,3-dihydropyran (50 mg) and p-toluensulfonic acid (10 mg). After stirring for 30 minutes at room temperature, the reaction mixture was neutralized with aqueous sodium bicarbonate and diluted with ethylacetate. After equilibration, the organic layer was washed with water and brine. Evaporation of the solvent gave an objective tetrahydropyranylether compound (113 mg).

IR$\nu_{max}^{film}$ cm$^{-1}$: 2950, 1775, 1490.

EXAMPLE 14

9-α-Hydroxy-11-α, 16-bis(tetrahydropyranyloxy)-20-methyl-cis-5-trans-14-prostadienoic acid methyl ester.

The tetrahydropyranyl compound (100 mg) obtained by the procedure of Example 13 was dissolved in dry toluene (5 ml) and 15% diisobutylaluminum hydride in toluene solution (3 ml) was added dropwise at −70° C. After stirring for 30 minutes at the same temperature, the mixture was quenched by adding carefully methanol until the evolution of gas ceased. The resulting mixture was allowed to warm to 0° C. and water (1 ml) was added. After stirring for another 30 minutes, the mixture was filtered and the filtrate was separated. The organic layer was washed with brine, dried over magnesium sulfate and evaporated to a hemiacetal (93 mg) as an oil. A mixture of 50% sodium hydride in mineral oil (96 mg) and dimethyl sulfoxide (10 ml) was stirred under nitrogen at 70–75° C. for 1 hr. To the methylsulfinyl carbanion thus obtained was added a solution of 4-carboxybutyltriphenylphosphonium bromide (443 mg) in dimethyl sulfoxide (5 ml) at 20° C. After 5 minutes, to this solutin was added a hemiacetal prepared above, in dimethyl sulfoxide (2 ml) and the resulting solution was stirred at room temperature for 3 hr. To the reaction mixture, was added a mixture of ethyl acetate and water and the organic layer was separated.

The aqueous phase was then acidified to pH 1 with diluted hydrochloric acid and was extracted with ethyl acetate. Evaporation of solvent gave an oil, which was dissolved in tetrahydrofuran and treated with ethereal diazomethane. After evaporation, the resulting residue was chromatographed on silica gel to give an objective methylester derivative (98 mg).

IR$\nu_{max}^{film}$ cm$^{-1}$: 3350, 2930, 1735, 1280.

EXAMPLE 15

9-α, 11-α, 16-Trihydroxy-20-methyl-cis-5-trans-14-prostadienoic acid methyl ester.

9α-Hydroxy-11-α, 16-bis(tetrahydropyranyloxy)-20-methyl-cis-5-trans-14-prostadienoic acid methyl ester (80 mg) obtained by the procedure of Example 14 was dissolved in a mixture of acetic acid-tetrahydrofuran-water (10:3:10) (10 ml) and heated at 50° C. for 3 hr. After evaporation, the residue was chromatographed on silica gel to give an objective triol compound (35 mg).

IR$\nu_{max}^{film}$ cm$^{-1}$: 3450, 2950, 1935, 1280

EXAMPLE 16

9-Oxo-11α,16-dihydroxy-20-methyl-cis-5-trans-14-prostadienoic acid methyl ester.

9-α-Hydroxy-11α,16-bis(tetrahydropyranyloxy)-20-methyl-cis-5-trans-14-prostadienoic acid methyl ester (95 mg) obtained by the procedure of Example 14 was dissolved in methylene chloride. To this solution was added a solution of two equivalent of Collins reagent in methylene chloride. After stirring at room temperature for 10 minutes, ether was added and the mixture was filtered through celite. The filtrate gave, after evaporation, a crude 9-oxo-11α,16-bis(tetrahydropyranyloxy)-20-methyl-cis-5-trans-14 prostadienoic acid methyl ester (88 mg).

IR$\nu_{max}^{film}$ cm$^{-1}$: 3450, 2950, 1740, 1280

The crude compound prepared above was dissolved in a mixture of acetic acid-tetrahydrofuram-water (65:10:35) (10 ml) and stirred at 45° C. for 3 hr. The reaction mixture was concentrated in vaccuo and to the residue was added ethylacetate and water. The organic layer was separated, washed with brine, dried and evaporated to give an oil, which was chromatographed on silica gel to afford the objective methyl prostate derivative.

IR$\nu_{max}^{film}$ cm$^{-1}$: 3450, 2995, 2950, 1740, 1730, 1480, 1380, 1250.

What we claim is:

1. A compound of the formula

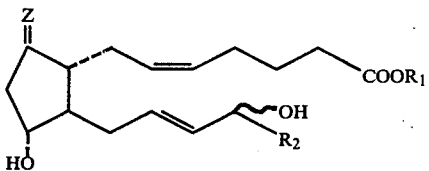

wherein
R$_1$ is hydrogen or C$_{1-4}$ alkyl,
R$_2$ is C$_{4-8}$ alkyl and >C=Z is >C=O

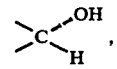

2. A pharmaceutical composition comprising as an active ingredient a compound of Claim 1 in an amount effective to treat or prevent a gastrointestinal ulcer and a pharmaceutically acceptable carrier.

3. A method of treating or preventing gastrointestinal ulcer which comprises administering a composition of claim 2 to a patient.

* * * * *